(12) United States Patent
Al-Zaydi et al.

(10) Patent No.: US 11,104,692 B1
(45) Date of Patent: *Aug. 31, 2021

(54) HETEROCYCLIC DIAZENYL PYRIDINONE COPPER(II) COMPLEXES AS PHARMACOLOGICAL ANTITUMOR AGENTS

(71) Applicant: King Abdulaziz University, Jeddah (SA)

(72) Inventors: Khadijah Mohamed Khalf Al-Zaydi, Jeddah (SA); Ahlam Ibrahim Difullah Al-Sulami, Jeddah (SA); Maram Talal J Basha, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/176,638

(22) Filed: Feb. 16, 2021

Related U.S. Application Data

(62) Division of application No. 17/026,418, filed on Sep. 21, 2020, now Pat. No. 10,975,102.

(51) Int. Cl.
*A61K 31/555* (2006.01)
*C07F 1/08* (2006.01)

(52) U.S. Cl.
CPC .............. *C07F 1/08* (2013.01); *C07B 2200/13* (2013.01)

(58) Field of Classification Search
CPC ........ A61K 31/555; A61K 31/30; A61P 35/00
USPC ........................................................ 514/186
See application file for complete search history.

*Primary Examiner* — Charanjit Aulakh
(74) *Attorney, Agent, or Firm* — W&C IP

(57) ABSTRACT

Heterocyclic diazenyl pyridinone copper(II)-based complexes are provided as pharmacological antitumor agents e.g. to treat lung cancer.

4 Claims, 9 Drawing Sheets

Figure 4A
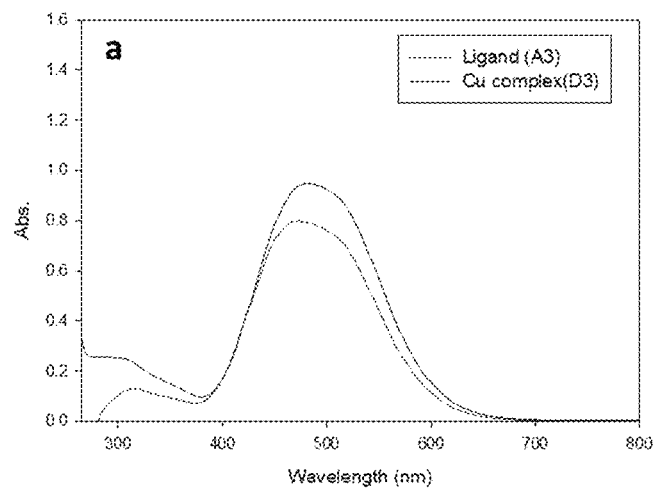
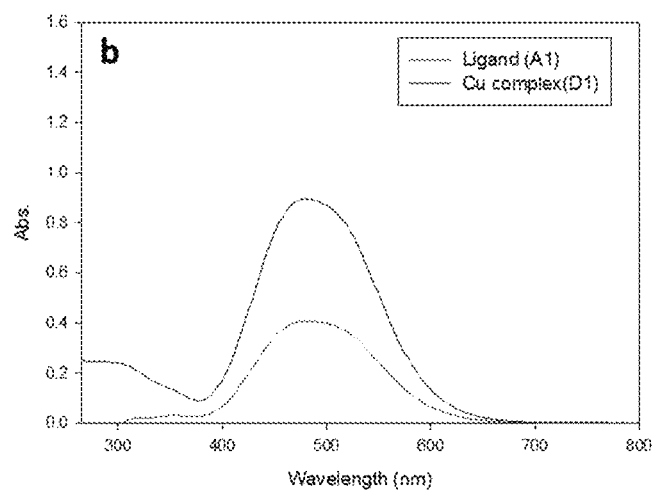
Figure 4B

Figure 5A
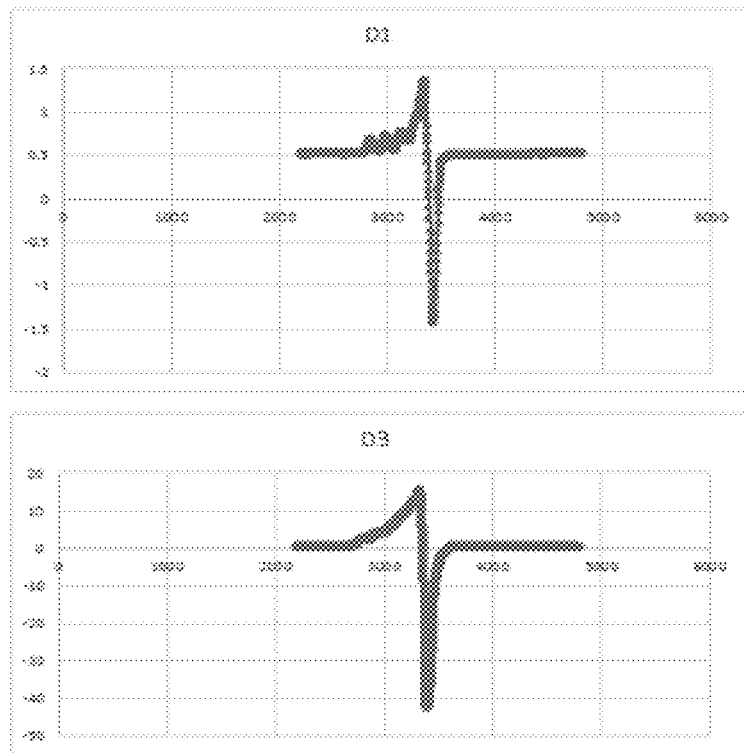
Figure 5B
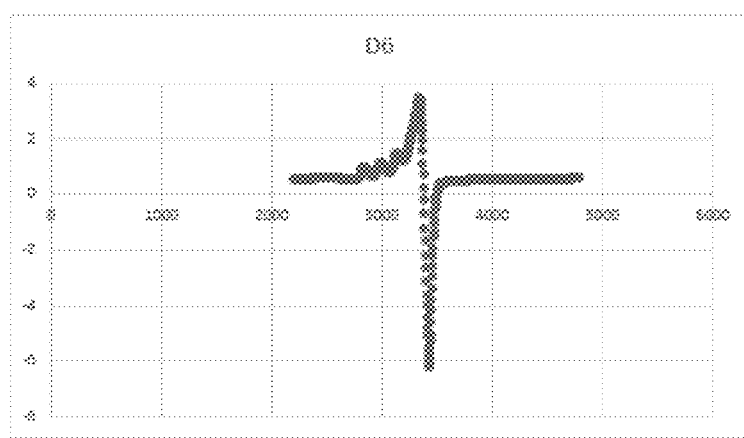
Figure 5C

HETEROCYCLIC DIAZENYL PYRIDINONE COPPER(II) COMPLEXES AS PHARMACOLOGICAL ANTITUMOR AGENTS

BACKGROUND OF THE INVENTION

Field of the Invention

The invention generally relates to anticancer agents. In particular, heterocyclic diazenyl pyridinone copper(II)-based complexes are provided as pharmacological antitumor agents e.g. to treat lung cancer.

Description of Related Art

In the past 40 years, remarkable increases in socioeconomic status have developed. During this societal growth and change, people's lifestyles have also been modified, and these modifications are believed to be responsible for increases in the incidence of many diseases, such as cancer [3]. Accordingly, the Saudi Health Council (SHC) has reported that the rise in the proportion of cancer types in the past decade is increasing the percentage of mortality due to cancer between 1990 and 2016 [4]. Thus, a significant challenge is to design new drugs that will be more selective for cancer cells at low cost.

A variety of metal complexes that have been investigated and combined with different moieties for chemotherapeutic treatment are shown in FIG. 1. Cisplatin (Cis-diamminedichloroplatinum) has been present in the worldwide market and used as an anticancer drug for many years. Several side effects, such as nephrotoxicity, hematologic toxicity, and neurotoxicity, limit its usage [3,5,6,16].

Remarkably, in vitro and in vivo results obtained with copper (II)-based complexes have received considerable attention [7-9]. Copper can undergo redox activity and competitively bind to a site occupied by other metals. However, it is essential as a cellular agent for many biological pathways, including cofactor activity in an enzyme catalytic process [1] and in apoptosis of various cancer cell lines with different modes of action. However, in contrast to other metal-based complexes, copper-based complexes with thiosemicarbazone ligands exhibit antitumor activity by inhibiting enzymatic activity [11,12].

Increasing evidence has confirmed the efficacy of copper compounds as antitumor drugs with a broad spectrum of activities and lower toxicity [7-8]. Copper complexes of benzimidazole exhibited inhibitory activity on SMMC7721-human liver, BGC823 human gastric, HCT116 human colon, and HT29 human colorectal cancer cell lines [11,13]. Moreover, a complex of Topo-I inhibitors, [Cu (N) L] Cl (N=phen, bipy or 5,50-dimethyl-2,20-bipyridine; L=doubly 5-triphenylphosphonium-methyl)-salicylaldehyde deprotonated hyde-benzoyl hydrazone, exhibits good cytotoxic activity against human lung cancer cells [14]. Bipyridyl ligands have the potential to make two nitrogen coordination bonds in exerting a cytotoxic effect on HL-60 human leukemia, MCF-7, HepG2, and NCI-H292 lung cancer cell lines [15].

Although some metal-based complexes with different modes of action have been suggested as cytotoxic agents, most of them suffer from causing many side effects, such as gastrointestinal toxicity and hematologic and bone marrow disorders [2]. In addition, they have a very short half-life in the body. Therefore, new drug candidates with a low $IC_{50}$ and fewer side effects are needed.

SUMMARY OF THE INVENTION

Provided herein are heterocyclic diazenyl pyridinone copper(II)-based complexes for use as pharmacological antitumor agents. The compounds exhibit excellent anti-cancer chemotherapeutic activity e.g. in lung cancer cells. Without being bound by theory, it is believed that these agents activate the cell death pathway in tumor cells.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

An object of the invention is to provide complexes having the general structural Formula I:

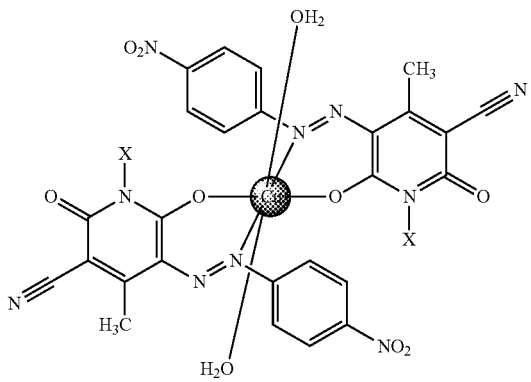

Formula I where X=a C1 to C20 hydrocarbon which is optionally substituted, and where X may be the same or different at both locations. One or more of these compounds may be present in a pharmaceutical composition with a pharmaceutical carrier (e.g., fluid (oil or aqueous), solid, etc.) deliverable to a human or other animal by a variety of routes for the treatment of cancers, such as lung cancer. Exemplary X substituents include butyl, hexyl or benzyl.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

Various embodiments of this disclosure will be described with the reference to the accompanying drawings.

FIG. 4A-C. UV-Vis spectra of Cu(II)-based complexes and their ligands using DMF solvent. A, A3 and D3; B, A1 and D1; C, A6 and D6.

FIG. 5A-C. EPR spectra of the complexes. A, D1; B, D3; C, D6.

DETAILED DESCRIPTION

Figure 1:
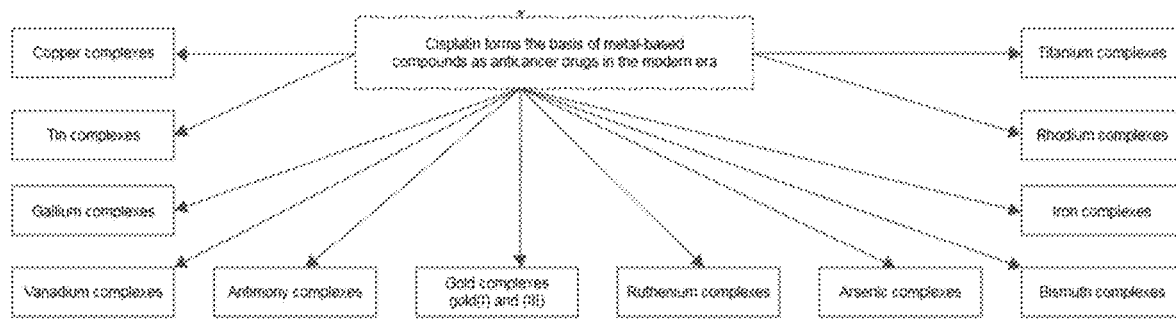
FIG. 1. Variety of metals used as complexes for chemotherapeutic treatment in the modern era.

Based on the unmet need in the art, new heterocyclic diazinyl pyridinone derivatives are provided. The derivatives are copper(II)-based complexes comprising nitro electron withdrawing groups and a variety of alkyl and/or aryl functional groups. The new complexes exhibit high activity against e.g. lung cancer cells, and thus show great promise as antitumor agents.

A generic structure of the complexes is shown in Formula I:

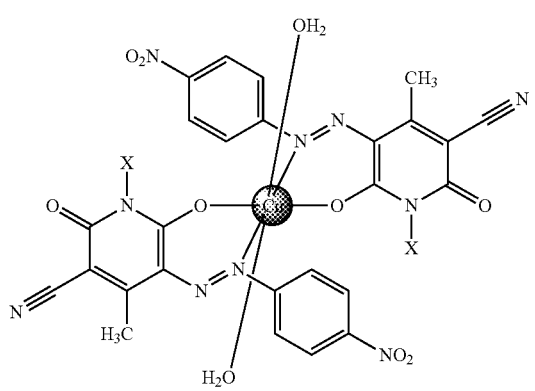

where X=a C1 to C20 hydrocarbon which is optionally substituted. In the examples below the same substituent X was used at both locations; however, in the practice of the invention, X will be a C1 to C20 hydrocarbon which optionally substituted and may be the same or different at the two locations.

C1 to C20 hydrocarbons include both aliphatic and aromatic groups, and may be substituted or unsubstituted.

Aliphatic hydrocarbons may be saturated or unsaturated, cyclic, linear or branched. Examples of aliphatic hydrocarbons include methyl, ethyl, propyl, isopropyl, n-butyl, s-butyl, t-butyl, 2-butenyl, 2-butynyl, pentyl, hexyl, heptyl, octyl, nonyl, etc.

Cyclic aliphatic hydrocarbons (cycloalkyls) is a subset of hydrocarbon and includes cyclic hydrocarbon groups of from e.g. 3 to 8 carbon atoms. Examples of cycloalkyl groups include cyclopropyl, cyclobutyl, cyclopentyl, norbornyl, and the like.

Aromatic (aryl) hydrocarbons include the simple aryl group phenyl (with the chemical formula $C_6H_5$), a group derived from benzene; the tolyl group, $CH_3C_6H_4$, which is derived from toluene (methylbenzene); the xylyl group, $(CH_3)_2C_6H_3$, which is derived from xylene (dimethylbenzene); the naphthyl group, $C_{10}H_8$, which is derived from naphthalene; etc.

The C1 to C20 hydrocarbon groups which include aliphatic and aromatic groups are optionally substituted. As used herein, the term "optionally substituted" may be used interchangeably with "unsubstituted or substituted". The term "substituted" refers to the addition of one or more substituents by replacement of a carbon atom or as an attachment to a carbon atom. In some embodiments, substituents are halogen, haloalkyl, alkyl, acyl, hydroxyalkyl, hydroxy, alkoxy, haloalkoxy, aminocarbonyl oxaalkyl, carboxy, cyano, acetoxy, nitro, amino, alkylamino, dialkylamino, alkylthio, alkylsulfinyl, alkylsulfonyl, alkylsulfonylamino arylsulfonyl, arylsulfonylamino, and benzyloxy. Additional examples include: substituted alkyl, aryl, cycloalkyl, etc. wherein one or more H atoms are replaced with halogen, haloalkyl, alkyl, acyl, alkoxyalkyl, hydroxy lower alkyl, carbonyl, phenyl, heteroaryl, benzenesulfonyl, hydroxy, lower alkoxy, haloalkoxy, oxaalkyl, carboxy, alkoxycarbonyl, alkoxycarbonylamino, aminocarbonyl (also known as carboxamido), alkylaminocarbonyl, cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical.

Cyclic and aromatic hydrocarbons may also be heterocyclic. Heterocyclic means an aliphatic or aromatic carbocycle in which from one to four carbons is replaced by a heteroatom selected such as N, O, or S. Heterocycles may also be optionally substituted. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

In some aspects, the C1 to C20 hydrocarbon is butyl, hexyl or benzyl.

The structures of exemplary complexes D1, D3 and D6 and their respective starting materials, A1, A3 and A6, are depicted in Scheme 1:

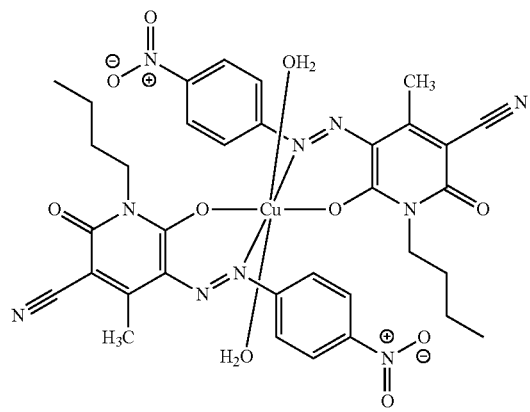

D1

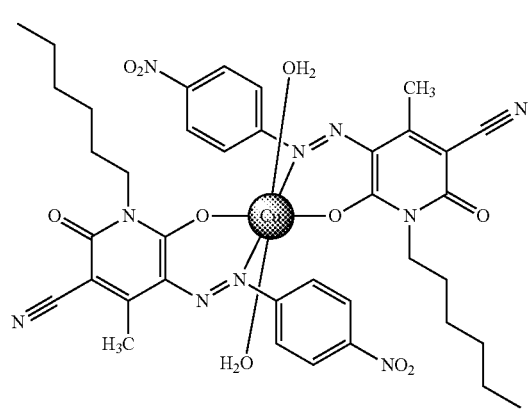

D3

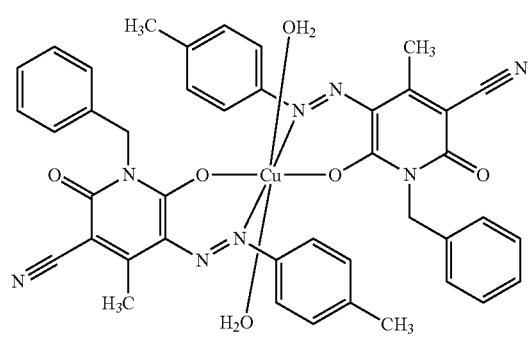

D6

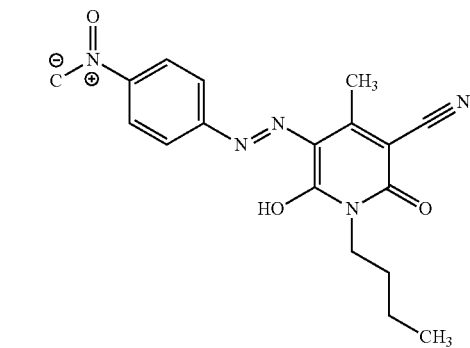

A1

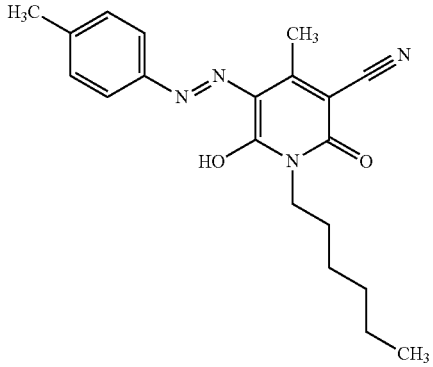

A3

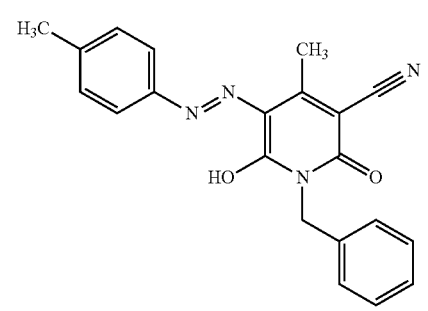

A6

Pharmaceutical Preparations

The compounds (complexes) described herein are generally delivered (administered) as a pharmaceutical composition. Such pharmaceutical compositions generally comprise at least one of the disclosed compounds, i.e. one or more than one (a plurality) of different compounds (e.g. 2 or more such as 2, 3, 4, 5, 6, 7, 8, 9, 10 or more) may be included in a single formulation. Accordingly, the present invention encompasses such formulations/compositions. The compositions generally include one or more substantially purified compounds as described herein, and a pharmacologically suitable (physiologically compatible) carrier, which may be aqueous or oil-based. In some aspects, such compositions are prepared as liquid solutions or suspensions, or as solid forms such as tablets, pills, powders, various dosage forms, and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Administration

The terms "administer", "administering" or "administration" in reference to a dosage form of the invention refers to the act of introducing the dosage form into the system of a subject in need of treatment.

Treatment can involve administering a therapeutically effective amount of a compound described herein to a patient diagnosed with a disease and may involve administering the compound to a patient who does or does not have active symptoms. Conversely, treatment may involve administering the compositions to a patient at risk of developing a particular disease, or to a patient reporting one or more of the physiological symptoms of a disease, even though a diagnosis of this disease may not have been made.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease. A therapeutic benefit is achieved with the amelioration of one or more of the physiological symptoms associated with the underlying disorder such that an improvement is observed in the patient, notwithstanding that the patient may still be afflicted with the underlying disorder.

The compositions comprising the complexes may be administered in vivo by any suitable route including but not limited to: inoculation or injection (e.g. intravenous, intraperitoneal, intramuscular, subcutaneous, intra-aural, intraarticular, intramammary, and the like), topical application (e.g. on areas such as eyes, skin, in ears or on afflictions such as wounds and burns) and by absorption through epithelial or mucocutaneous linings (e.g., nasal, oral, vaginal, rectal, gastrointestinal mucosa, and the like). Other suitable means include but are not limited to: inhalation (e.g. as a mist or spray), orally (e.g. as a pill, capsule, liquid, etc.), intravaginally, intranasally, rectally, as eye drops, etc. In preferred embodiments, the mode of administration is by injection, e.g. intravenous or by inhalation into the lungs.

In addition, the compositions may be administered in conjunction with other treatment modalities such as substances that boost the immune system, various chemotherapeutic agents, surgery, radiation therapy, etc. When a dosage form of the invention is given in combination with one or more other active agents (in their respective dosage forms), "administration" and its variants are each understood to include concurrent and/or sequential introduction of the dosage form and the other active agents. Administration of any of the described dosage forms includes parallel administration, co-administration or sequential administration. In some situations, the therapies are administered at approximately the same time, e.g., within about a few seconds to a few hours of one another.

The subjects that are treated can be any that have or are suspected of having cancer, especially lung cancer. The subject may be of any gender or age. Generally, the subject is a mammal, typically a human, although veterinary applications of this technology are also encompassed.

The dose of a complex that is administered may be any that is suitable for the type of cancer, the particular patient, etc. Generally, the dose ranges from about 1 to about 500 mg/kg of body weight, such as about 1, 10, 20, 30, 40, 50, 60, 70, 80, 90, 100, 150, 200, 250, 300, 350, 400, 450 or 500 mg/kg, or even more, including all single digit integers between these values. In some aspects, the concentration of the samples may range from 0.78 to 100 µg/ml, based on our analysis using MTT assay.

Types of Cancers that are Treated

The compounds provided herein can be used for treating cancer in a patient, the method comprising administering to the patient a therapeutically effective amount of a compound of formula I. In some embodiments, the type of cancer can be, but is not limited to: ovarian, pancreatic, renal cell, breast, prostate, lung, hepatocellular carcinoma, glioma, leukemia, lymphoma, colorectal cancers, or sarcomas, as well as other types of cancers that are listed e.g. in issued U.S. Pat. No. 10,759,790, the complete contents of which is hereby incorporated by reference in entirely. In some aspects, the cancer is lung cancer.

Other Aspects

Also provided herein are methods of killing cancer cells by contacting the cancer cells with a compound disclosed herein. The cells may be in vitro or in vivo. In some aspects, the cancer cells are as described elsewhere herein. In further aspects, the cancer cells are lung cancer cells.

It is to be understood that this invention is not limited to particular embodiments described herein above and below, and as such may, of course, vary. It is also to be understood that the terminology used herein is for the purpose of describing particular embodiments only and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc. . . .".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Example

Figure 2:
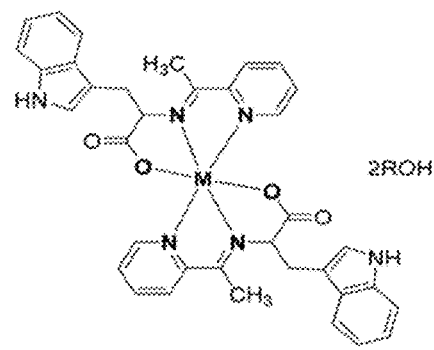
FIG. 2. Structure of metal-based amino acid complexes (M=Cu, Zn, Cd).

Due to the coordination of transition-metal ion complexes via an N—N—S tridentate ligating system, iron and copper complexes of thiosemicarbazones [17] have been studied for biological applications including antitumor [18], antifungal [19], antiviral [20], antibacterial [21], antifilarial [22] and antimalarial activities [23]. Heterocyclic moieties with highly dense electrons coordinated at the centers of metal-based complexes have received considerable attention as pharmacological agents and have been used as antibacterial, antifungal, and antiviral agents [24,25]. Cu, Zn, and Cd transition metal coordination complexes which form a type of 4N+2O neutrality complex inhibit cellular proliferation and have anticancer activity on breast cancer cells (MDA-MB-231). Remarkably, the inhibitory activity is three times higher than the widely used drug cisplatin in human breast and human lung carcinoma cells FIG. 2.

Figure 3:
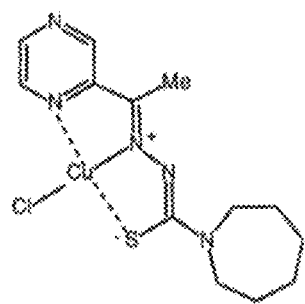
FIG. 3. Structure of tri-dentate thiosemicarbazone (N—N—S) coordinated on the Cu(II)-complex.

On the other hand, heterocyclic thiosemicarbazone ligands have gained interest due to their inhibitory action ascribed to the coordination of iron by a heterocyclic thiosemicarbazone's N—N—S tri-dentate ligating system. Copper complexes with thiosemicarbazone ligands have antitumor activity by inhibiting enzymatic activity FIG. 3 [11,12, 17].

However, the evidence has presented that hindering the thiosemicarbazone directly affects the ability of the compound to function as a chelating agent with metal ions and completely destroys or reduces its strength as therapeutic activity [27].

Copper complexes usually are water-insoluble. Consequently, the use of suitable sizes of polymers/nanoparticles containing the copper complexes can increase the cellular distribution with respect to targeting tumor cells with a reduction of the toxicity in healthy cells. Many side effects, including gastrointestinal toxicity, hematologic, and bone marrow disorders, are potentially associated with the Cu-based chemotherapeutic agents [2]. Therefore, developing new drug candidates with a low $IC_{50}$ and fewer side effects is of great interest.

This example describes the synthesis and characterization of heterocyclic diazenyl pyridinone copper(II)-based complexes as potential pharmacological antitumor agents. Their potential to act as anti-cancer chemotherapeutic agents, as well as their impact on the cell death pathway, was investigated in A-590 human lung cancer cell lines.

The copper(II)-based complexes (D1, D3, D6, see Scheme 1) were synthesized by the following general method: (2 mmol) of each ligand (A1, 0.412 g), (A3, 0.445 g), (A6, 0.543 g) were dissolved in 20 ml of hot ethanol. Then, a solution of the $CuCl_2$ salt (0.171 g, 1 mmol) was added dropwise with constant stirring, followed by adding few drops of an aqueous solution of sodium hydroxide NaOH (0.5 M) to adjust the pH at 8. The mixture gently refluxed for 2 h at 50° C. Under reduced pressure, the volume condensed to half of the initial amount. Then, solid of Cu(II)-based complexes precipitated upon slow cooling at room temperature, and the precipitate was filtered off, washed with cold ethanol (10 mL) followed by diethyl ether (10 mL), and dried under vacuum over anhydrous $CaCl_2$). The crude products (Cu(II) complexes) were recrystallized from the solvent DMF at room temperature.

4.2 Result and Discussion
4.2.1 FT-IR Spectra

The FT-IR spectra of the free ligands of (A1, A3, A6) and the respective Cu(II)-based complexes (D1, D3, D6) in the solid-state revealed the coordination mode of the ligands and complexes, respectively. The stretching vibration of the free ligands v(—OH) at 3434-3460 $cm^{-1}$ was not observed in the IR spectra of the complexes, suggesting the deprotonation of the hydroxyl group and formation of M-O bonds [28,29]. However, bands between 1617-1626 $cm^{-1}$ in the free ligands are assigned to v(—CN), and they are shifted to lower wavenumbers in the complexes due to the coordination of the nitrogen atom of the diazenyl to the metal ion center [30,31]. The strong band assigned to v(N=N) at 1511 $cm^{-1}$ in the spectra of the free ligands is shifted to higher frequencies in all complexes at 1544 $cm^{-1}$, indicating its involvement in the coordination of the ligands to the metal ions [32]. The bands assignable to v(CN) at 2250 $cm^{-1}$ shifted to the lower wavenumber 2216 $cm^{-1}$ in the complex.

Moreover, in the far IR spectra of all complexes, there are new bands observed in the region of 580-400 $cm^{-1}$, which are absent in the spectra of the free ligands. The band observed between 464-495 $cm^{-1}$ represents the v(M-N) bond. Also, the bands at 530 and 572 $cm^{-1}$ are presenting the v(M-O) band, which gives conclusive evidence concerning the bonding of nitrogen and oxygen to the metal ions [33]. Therefore, the IR spectra indicate that the ligands coordinate through the deprotonated 0 and azo N.

4.2.2 UV-Vis Spectra

Figure 4C:
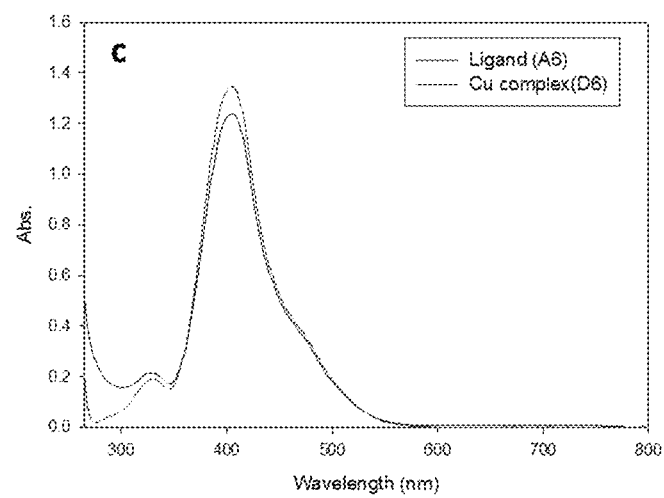

The precursors of the free ligands of (A1, A3, A6) with corresponding Cu(II)-based complexes (D1, D3, D6) were characterized by a dark orange and brown color, respectively. The UV-Vis charts (FIG. 4A-C) showed that all samples gave similar absorption bands with slight differences in their intensities likely due to the similarity of their chemical compositions. The high absorbance intensity in the range of 380-500 nm with a maximum absorbance at 470 nm for the precursors (A3) and 480 nm for the complex (D3) confirm the presence of metal-ligand charge transfer and successful loading of the ligand on the Cu(II) metal center (FIG. 4B). However, the π-π electronic transitions in the conjugated aromatic system are responsible for a significant shift toward a long wavelength region, indicating the presence of a benzene aromatic group (FIG. 4C, [34]). On the other hand, weak absorbance in the range of 200-300 nm is associated with n-π (electronic transitions and indicates the presence of functional groups in the ligand and the complex, for example, hydroxyl and carbonyl groups.

4.2.3 EPR Spectra

The EPR spectra of the (D1, D3, D6) complexes were recorded in DMF solution at LNT (77K). All complexes exhibited a typical four-line spectral pattern, assignable to monomeric copper (II) complexes [35]. From the observed g values, $g_{prep} < g_{\|} < 2$, it is apparent that the unpaired electron lies predominantly in the $d_{x2-y2}$ orbital giving $^2B_1g$ as the ground state [36]. This also indicates the ionic nature of the metal-ligand bond in the complex. Moreover, the higher $g_\|$ values indicate a slight distortion from regular planarity [37,38] (FIG. 5A-C).

4.2.4 Single-Crystal X-Ray Structure Determination

Figure 6:
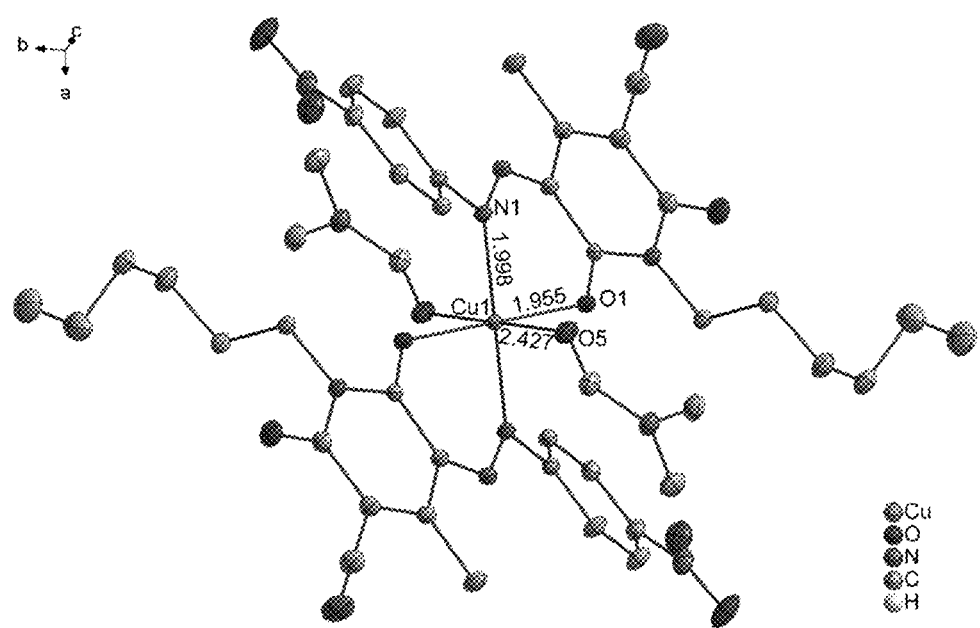
FIG. 6. Representation of the molecular structure of the D3 complex. Thermal ellipsoids are drawn with 50% probability.
Figure 7:
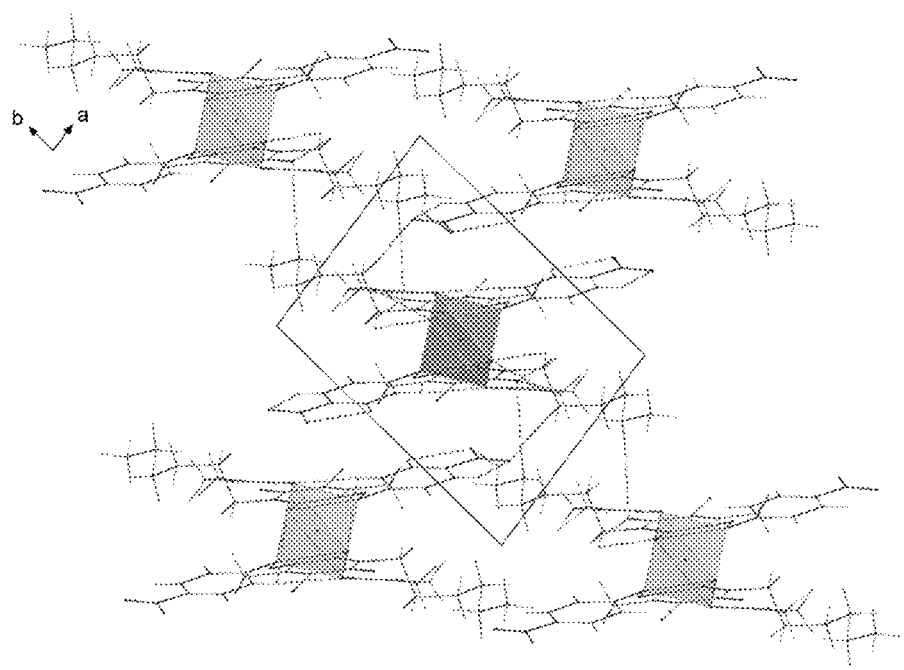
FIG. 7. D3 complex molecules packed along [110] via intermolecular H-bonding to form a 3D extended supramolecular network.

X-ray determination showed that the structure adopts triclinic lattice with P$\bar{1}$ (2) symmetry (see Table 1). In this compound, the octahedral coordination environment of Cu is completed by two L ligands and two co-crystallized DMF molecules. The ligands are attached to the Cu-atom by a nitrogen atom of the diazenyl-group and an oxygen atom of the oxidaneyl group with d(Cu—N4)=1.998(1) Å and d(Cu—O1)=1.955(1) Å (FIG. 6). The DMF solvent molecules are coordinating the Cu atom through oxygen atoms with d(Cu—$O_5$)=2.427(1) Å. The compound also has intra- and intermolecular hydrogen bonding with C—O . . . H distances ranging between 2.336(1) Å to 2.722(1) Å. The extended supramolecular framework is formed by packing of the molecules along [110] with the help of intermolecular H-bonding (see FIG. 7).

TABLE 1

Crystallographic data and structure refinement details of D3 complex.

| | |
|---|---|
| Complex code | D3 |
| Formula | $C_{44}H_{54}CuN_{12}O_{10}$ |
| T/K | 120 |
| M/g·$mol^{-1}$ | 974.54 |
| Crystal system | Triclinic |
| Space group | P-1 (2) |
| a/Å | 8.7981(3) |
| b/Å | 11.3934(4) |
| c/Å | 11.8737(4) |
| α/° | 88.133(1) |
| β/° | 79.305(1) |
| γ/° | 82.444(1) |
| V/$Å^3$ | 1159.35(7) |
| Z | 1 |
| $\rho_{calc}$/g·$cm^{-3}$ | 1.396 |
| μ/$mm^{-1}$ | 0.542 |
| Reflections | 114302 |
| $R_{int}$ | 0.0431 |
| Parameters | 308 |
| $R_1$ [I > 4σI][a] | 0.0364 |
| wR2[all data] | 0.1045 |
| S[c] | 1.071 |
| Max./min./e·$Å^3$ | 0.661/−0.787 |

[Cu(L)$_2$(dmf)$_2$] The crystal structure of Cu-complex (D3) using the ligand L (A3), (E)-1-hexyl-4-methyl-5-((4-nitrophenyl)diazenyl)-6-($\lambda^1$-oxidaneyl)-2-oxo-1,2-dihydropyridine-3-carbonitrile).

4.2.5 Data Analysis of Cytotoxic Activity Test

D1, D3 and D6 were tested against a normal cell line of human primary hepatocytes, THLE-2 (ATCC). Cells were maintained at sub-confluency at 37° C. in humidified air containing 5% of $CO_2$. The concentration of the samples ranged from (100 to 0.78 μg/ml) using the MTT assay.

Table 2 shows the effect of complexes (D1, D3, D6) on the normal cell line. The data showed that the complexes were safe (not toxic to the cells) even at high concentrations. This result showed that the tumor-specificity for complex D3 as safe to a large extent on the human normal hepatocytes THLE-2.

Figure 8A:
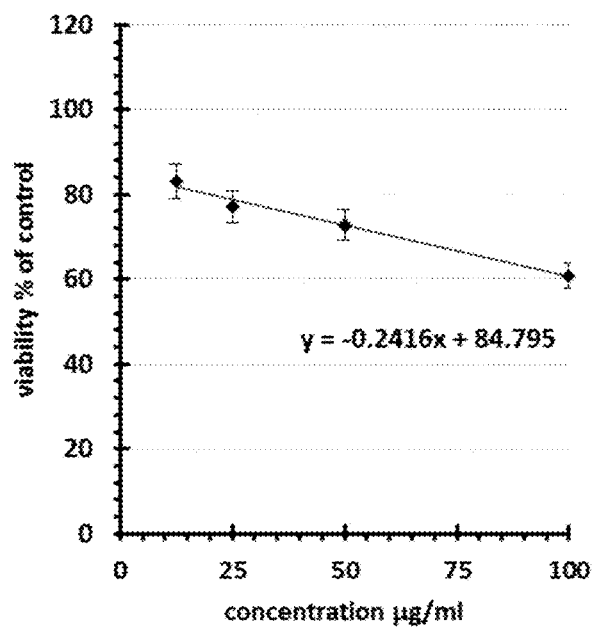
FIG. 8A-C. Anti-tumor efficiency against the A-590 human lung carcinoma cells for A, D1; B, D3; and C, D6.
Figure 8B:
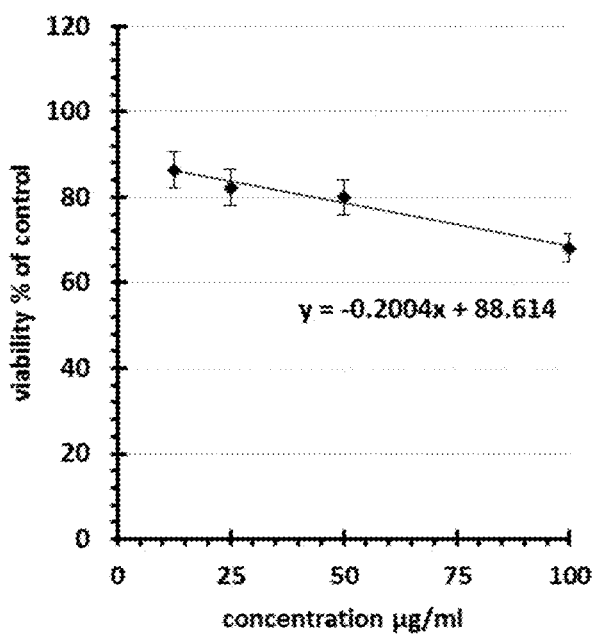
Figure 8C:
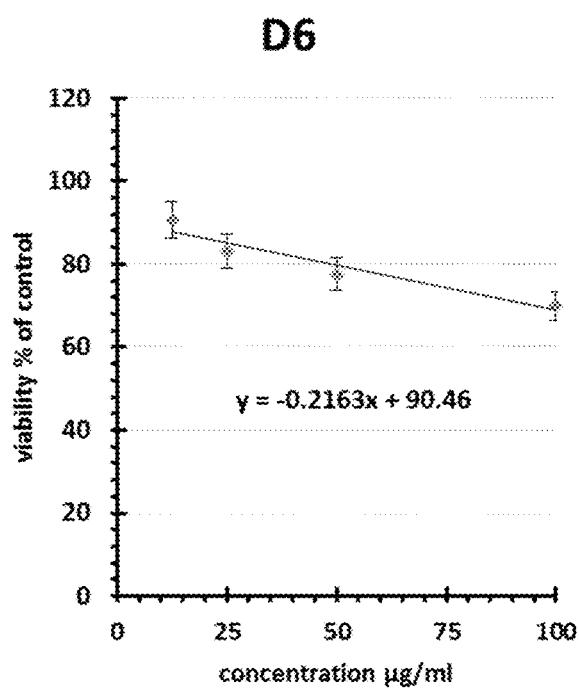

These promising results showing a higher anti-tumor efficiency for all tested drugs (D1, D3, D6) against the A-590 human lung carcinoma cells. Further, the agents are non-cytotoxic as well, $IC_{50}>100$ µg/ml (FIG. 8A-C).

TABLE 2

The effect of D1, D3, D6 complexes on normal THLE-2 human cells correlated with the cytotoxicity effects of the complexes against the A-590 human lung carcinoma cells

| complex Code | A-590 human lung carcinoma cells | | THLE-2 human normal hepatocytes | |
|---|---|---|---|---|
| | Mean $IC_{50}$ (µg/mL) | ±SE | Mean $IC_{50}$ (µg/mL) | ±SE |
| D1 | 28.76 | 1.95 | 144.00 | 9.94 |
| D3 | 20.64 | 9.90 | 192.69 | 13.30 |
| D6 | 4.71 | 0.02 | 187.08 | 12.91 |

$LC_{50}$: Lethal concentration of the sample which causes the death of 50% of cells in 48 hrs
The calculated $IC_{50}$: is represented [in f, µg/ml, mean ± SE]

REFERENCES

[1] Marzano, C., Pellei, M., Tisato, F., and Santini, C., *Anti-Cancer Agents in Med. Chem.*, 2009, 9, 185
[2] Kodama, Y., Fumoto, S., Nishi, J., Nakashima, M., Sasaki, H., Nakamura, J., and Nishida, K., *Biol. Pharm. Bull.*, 2008, 31, 1049
[3] Anand, P., Kunnumakkara, A. B., Sundaram, C. Harikumar, K. B. Tharakan, S. T., and Lai, O. S., *Pharmaceutical Research*, 2008, 25, 2097
[4] Mohammad, A. Althubiti., and Mohamed, M. Nour Eldein., *Saudi Med. J.*, 2018, 39, 1259
[5] Zhang, C. X., and Lippard, S. J., *Curr. Opin. Chem. Biol.*, 2003, 7, 481
[6] Johnstone, T. C., Park, G. Y., and Lippard, S. J., *Anticancer Research*, 2014, 34, 471
[7] Manjunath, M., Kulkarni, A. D., Bagihalli, G. B., Malladi, S., and Patil, S. A., *J. Mol. Struct.*, 2017, 1127, 314.
[8] Hranjec, M., Starčević, K., Pavelić, S. K., Lučin, P., Pavelić, K., and Karminski Zamola, G., *Eur J Med Chem.*, 2011, 11, 5200.
[9] Liu, S., Wei, W., Shi, K., Cao, X., Zhou, M., and Liu, Z., *J. Med. Chem.*, 2010, 202, 991.
[10] Badea, M., Calu, L., Chifiriuc, M. C., Bleotu, C., Marin, A., Ion, S., Ioniă, G., Stanică,
[11] N., MaruTescu, L., Lazar, V., Marinescu, D., and Olar, R. J., *J. Therm. Anal. calorim.*, 2014, 118, 1145
[11] Beckford, F. A., Shaloski, M. Jr., Leblanc, G., and Thessing, J., Lewis-Alleyne, L. C, Holder, A. A, Li, L., and Seeram, N. P., *Dalton Trans.*, 2009, 48, 10757.
[12] Liberta, A. E., and West, D. X., *Biometals*, 1992, 5, 1
[13] Zhao, Ja., Zhi, S., Yu, H., Mao, R., Hu, J., Song, W., and Zhang, J., *RSC Advances*, 2017, 7, 51162
[14] Chew, S. T., Lo, K. M., Lee, S. K., Heng, M. P., Teoh, W. Y., Sim, K. S., and Tan, K. W., *Eur. J. Med. Chem.*, 2014, 76, 397
[15] dos Santos Silva, T. D., Bomfim, L. M., da Cruz Rodrigues, A. C. B., Dias, R. B., Sales, C. B. S., Rocha, C. A, G., Soares, M. B. P., Bezerra, D. P., de Oliveira Cardoso, M. V., Leite, A. C. L., and Militao, G. C. G., *Toxicol Appl Pharmacol*, 2017, 329, 212

[16] Ndagi, U., Mhlongo, N., and Soliman, M. E., *Drug Des. Devel. Ther.*, 2017, 3, 599
[17] Liberta, A. E., and West, D. X., *Biometals*, 1992, 5, 121.
[18] Antholine, W. E., Knight, J., and Peterin, D. H., *Inorg Chem*, 1977, 16, 569.
[19] Mittal, S. P., Sharma, S K., Singh, R. V., and Tandon, J. P., *Curr. Sci.*, 1981, 50, 483.
[20]13. Shipman, C., Smith, S. H., Drach, G. C., and Klayman, D. L., *Antimicrob Agents Chemother*, 1981, 19, 682.
[21] Dobek, A. S., Klayman, D. L., Dickson, E. T., Scovill, J. P., and Tramont, E. C., *Antimicrob Agents Chemother,* 1980, 18, 27.
[22] Klayman, D. L., Lin, A. J., and McCall, J. W., *J. Med. Chem.*, 1991, 34, 1422.
[23] Klayman, D. L., Bartosevich, J. F., Griffin, T. S., Mason, C. J., and Scovill, J. P., *J. Med. Chem.*, 1979, 22, 862.
[24] Manjunath, M., Kulkarni, A. D., Bagihalli, G. B., Malladi, S., and Patil, S. A., *J. Mol. Struct.*, 2017, 1127, 314
[25] Badea, M., Calu, L., Chifiriuc, M. C., Bleotu, C., Marin, A., Ion, S., Ioniă, G., Stanică, N., Măruescu, L., Lazăr, V., Marinescu, D., and Olar, R. J., *J. Therm. Anal. calorim.*, 2014, 118, 1145
[26] Zhang, N., Fan, Y., Zhang, Z., Zuo, J., Zhang, P., Wang, Q., Liu, S., and Bi, C., *Inorg. Chem. Commun.*, 2012, 22, 68
[27] Scovill, J. P., Klayman, D. L., Lambrose, C., Childs, G. E., and Notsch, J. D., *J. Med. Chem.*, 1984, 27, 87
[28] Bansal, S. K., Tikku, S., and Sindhu, R. S., *J. Ind. Chem. Soc.*, 1991, 86, 566.
[29] Mostafa, S. I., *Polyhedron*, 1992, 11, 2997.
[30] Larabi, L., Harek, Y., Reguig, A., and Mostafa, M. M., *J. Serb. Chem. Soc.*, 2003, 68, 85.
[31] Dehghanpour, S., Bouslimani, N., Welter, R., and Mojahed, F., *polyhedron*, 1996, 15, 1283.
[32] Mohamed, G. G., Zayed, M. A., and El-Gamel, N. E. A., *Spectrochim. Acta A*, 2002, 58, 3167.
[33] Zaki, Z. M., Haggag, S S., and Soayed, A. A., *Spectrosc. Lett.*, 1998, 31, 757.
[34] Masayoshi. Nakahara: "The Science of Color", Baifukan, 2002, p. 108
[35] Bertini, I., Ganti, G., and Grassi, R., *Inorg, Chem.*, 1980, 19, 2189.
[36] Sakaguchi, U., and Addison, A. W., *J. Chem. Soc. Dalton Trans.*, 1979, 600.
[37] Yokoi, H., and Addison, A. W., *Inorg, Chem.*, 1977, 16, 1341.
[38] Annaraj, J. P., Ponvel, K. M., and Athappan, P., *Trans. Met. Chem.*, 2004, 29, 722

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of killing lung cancer cells, comprising contacting the lung cancer cells with a compound of Formula I:

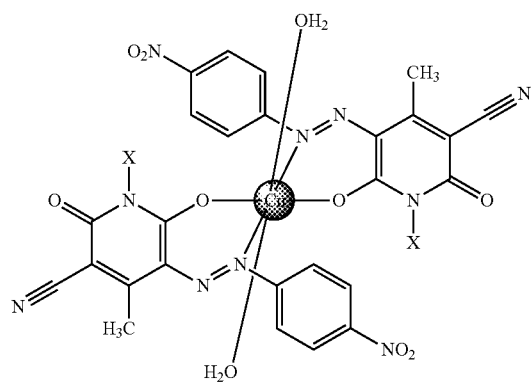

Formula I where X=a C1 to C20 hydrocarbon which is optionally substituted.

2. The method of claim 1, wherein X=butyl, hexyl or benzyl.

3. A method of treating lung cancer in a subject in need thereof, comprising administering to the subject a compound of Formula I:

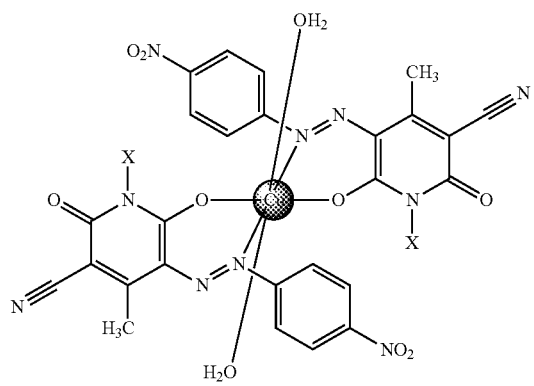

Formula I where X=a C1 to C20 hydrocarbon which is optionally substituted.

4. The method of claim 3, wherein X=butyl, hexyl or benzyl.

* * * * *